US008339597B2

(12) United States Patent
Dal Negro et al.

(10) Patent No.: US 8,339,597 B2
(45) Date of Patent: Dec. 25, 2012

(54) CHEMICAL/BIOLOGICAL SENSOR EMPLOYING SCATTERED CHROMATIC COMPONENTS IN NANO-PATTERNED APERIODIC SURFACES (75) Inventors: Luca Dal Negro, Cambridge, MA (US); Svetlana V. Boriskina, Winchester, MA (US); Fiorenzo Omenetto, Wakefield, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 13/192,757

(22) Filed: Jul. 28, 2011

(65) Prior Publication Data
US 2011/0285991 A1 Nov. 24, 2011

Related U.S. Application Data (63) Continuation of application No. PCT/US2010/022701, filed on Feb. 1, 2010.

(60) Provisional application No. 61/206,382, filed on Jan. 30, 2009.

(51) Int. Cl.
*G01J 3/44* (2006.01)
(52) U.S. Cl. ...................................................... 356/301
(58) Field of Classification Search .................... 356/301
See application file for complete search history.

(56) References Cited

U.S. PATENT DOCUMENTS

| 4,676,640 | A  | * | 6/1987 | Briggs ........................ 356/317 |
| 6,989,897 | B2 | * | 1/2006 | Chan et al. ..................... 356/301 |
| 2005/0213868 | A1 | * | 9/2005 | Cunningham .................. 385/12 |
| 2007/0042505 | A1 | * | 2/2007 | Israel et al. .................... 436/518 |
| 2010/0085566 | A1 | * | 4/2010 | Cunningham ................ 356/301 |

* cited by examiner

*Primary Examiner* — Layla Lauchman
(74) *Attorney, Agent, or Firm* — BainwoodHuang (57) ABSTRACT A label-free multiplexed sensing platform is based on light interaction with aperiodic photonic structures with an advantage of a broadband operation. Multiple-scattering-induced "fingerprinting" colorimetric signatures can be used as a transduction mechanism. Aperiodic sensing platforms can operate in the infrared to provide an overlap with spectral fingerprints of biological molecules. Miniaturized optical biosensors may be based on engineered colorimetric scattering signatures (structural color), sharp spectral features, non-uniform angular distributions of scattered light, and broadband manipulation of the local density of states in nano-textured scattering surfaces with deterministic aperiodic order. The biosensors can be fabricated in semiconductor, metal, low- and high-index dielectric platforms using standard nanofabrication techniques such as electron-beam lithography, ion-beam milling, etc, and can be replicated over large areas by standard nano-imprint lithography.

26 Claims, 8 Drawing Sheets

CHEMICAL/BIOLOGICAL SENSOR EMPLOYING SCATTERED CHROMATIC COMPONENTS IN NANO-PATTERNED APERIODIC SURFACES

STATEMENT REGARDING FEDERALLY SPONSORED RESEARCH OR DEVELOPMENT

This invention was made with Government Support under Contract No. W911NF-07-1-0618 awarded by the Army Research Office. The Government has certain rights in the invention.

BACKGROUND

Scattering of photons by periodic photonic structures gives rise to a variety of interesting physical effects including manipulation of spontaneous emission, formation of forbidden photonic gaps, resonantly enhanced transmission through sub-wavelength apertures, and emission profile shaping, which can be exploited for sensor applications enabling direct label-free detection of various molecular targets in real time. It has been demonstrated that these effects can also be observed in the structures with deterministic-aperiodic (e.g., quasi-periodic) morphologies that do not possess translational periodicity. Furthermore, phenomena inherent to random structures, such as light localization, have been demonstrated in aperiodic photonic structures with high degrees of structural complexity.

The periodic-grating-based biosensors demonstrated to date usually track the change in the angular intensity distribution of the diffracted light or the frequency shift of the scattering or back-reflection resonance. Double-periodic gratings having a different period in each lateral direction, which feature resonant reflection peaks at two specific wavelengths, depending on the polarization of incident electromagnetic wave, have also been proposed for biomolecule detection using two distinct sensing modalities. A resonant reflection peak excited by one polarization of incident light has been tuned to coincide with the excitation wavelength of a fluorophore, while the shift of the peak generated by the light of orthogonal polarization has been used for label-free detection of adsorbed biomolecules. Analogously, sensors based on periodic photonic crystals with or without defects can detect the change in the refractive index of the ambient gas/liquid or the presence of infiltrated nanoparticles by monitoring the frequency shifts of high-Q factor optical resonances (corresponding to either band edge or defect modes) of the PhCs structures. Modification of the local density of states (LDOS) at selected wavelengths corresponding to the high-Q modes in periodic photonic crystals can also be used for enhancing signal from fluorophores. Finally, periodic gratings of metal nanoparticles with a period optimized to produce a sharp scattering resonance accompanied by a resonant enhancement of the near-field intensity at a selected wavelength owing to formation of photonic-plasmonic modes have been used for enhancing fluorescent and Raman signal as well as the IR absorption of biological molecules.

SUMMARY

The present disclosure is directed to a label-free multiplexed sensing platform based on light interaction with aperiodic photonic structures. Multiple sensing modalities are demonstrated with periodic photonic structures combined in aperiodic platforms, with an advantage of a broadband operation. Furthermore, multiple-scattering-induced "fingerprinting" colorimetric signatures of aperiodic arrays can be used as an additional novel transduction mechanism. Aperiodic sensing platforms can also be engineered to operate in the IR part of the electromagnetic spectrum, providing an overlap with the spectral fingerprints of many important biological molecules.

Miniaturized multiplexed optical biosensors may be based on engineered colorimetric scattering signatures (structural color), sharp spectral features, non-uniform angular distributions of scattered light, and broadband manipulation of the local density of states in nano-textured scattering surfaces with deterministic aperiodic order. These designed surfaces can be used as novel versatile bio-recognition platforms with high sensitivity to local refractive index variations and the presence of molecules/nano-objects on their surfaces. These novel types of biosensors can be fabricated in semiconductor, metal, low- and high-index dielectric platforms by using standard nanofabrication techniques such as electron-beam lithography, ion-beam milling, etc, and can be replicated over large areas by standard nano-imprint lithography. Combining multiple sensing modalities on the same platform and covering a wide spectral range offers a performance improvement over conventional periodic sensing platforms and provides exciting opportunities for a variety of high throughput lab-on-a-chip applications, including medical diagnostics, bio-hazard detection, and environmental sensing.

A specific configuration of planar deterministic aperiodic sensing platform can be generated by arranging identical unit cells according to simple deterministic algorithms based on the alternation of 1D deterministic aperiodic inflation rules (e.g., Fibonacci rule) along both orthogonal directions. Alternatively, an aperiodic structure with broadband scattering characteristics can be engineered by using automated global optimization techniques. A unit cell can be a nano-pillar, a deposited particle, or a nano-hole of an arbitrary shape, e.g., circular cylindrical, elliptical, square, triangular, etc, depending on specific applications needs. These novel types of biosensors can be fabricated in semiconductor, metal, low- and high-index dielectric platforms (or their combination) by using standard nanofabrication techniques such as electron-beam lithography, ion-beam milling, etc, and can be replicated over large areas by standard nano-imprint lithography. They can also be produced by microreplication of a master sensor surface structure on plastic films. We have also demonstrated a possibility of fabricating aperiodic sensing platforms from silk by pouring silk solution onto the lithographically-fabricated masters and allowing it to dry. The aperiodic sensor structures can be easily integrated with microfluidics for a controllable delivery of targets to the sensor area. In addition, planar aperiodic sensor structures are compatible with current microarray-based infrastructures that are most widely used for high throughput bimolecular interaction analysis.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

DETAILED DESCRIPTION

The entire disclosure of U.S. Provisional Application 61/206,382 is incorporated by reference herein.

Figure 1:
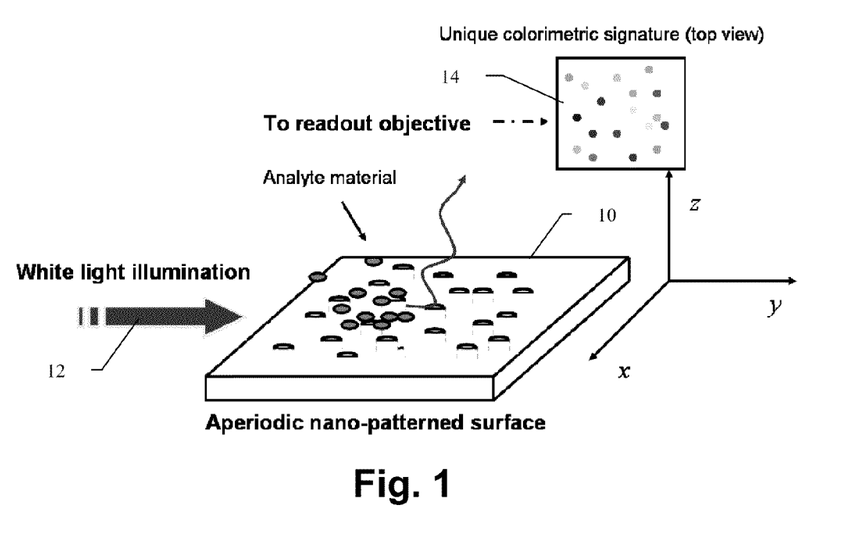
FIGS. 1 and 2 show simplified schematic diagrams of a colorimetric sensor based on an aperiodically nano-patterned planar surface.
Figure 2:
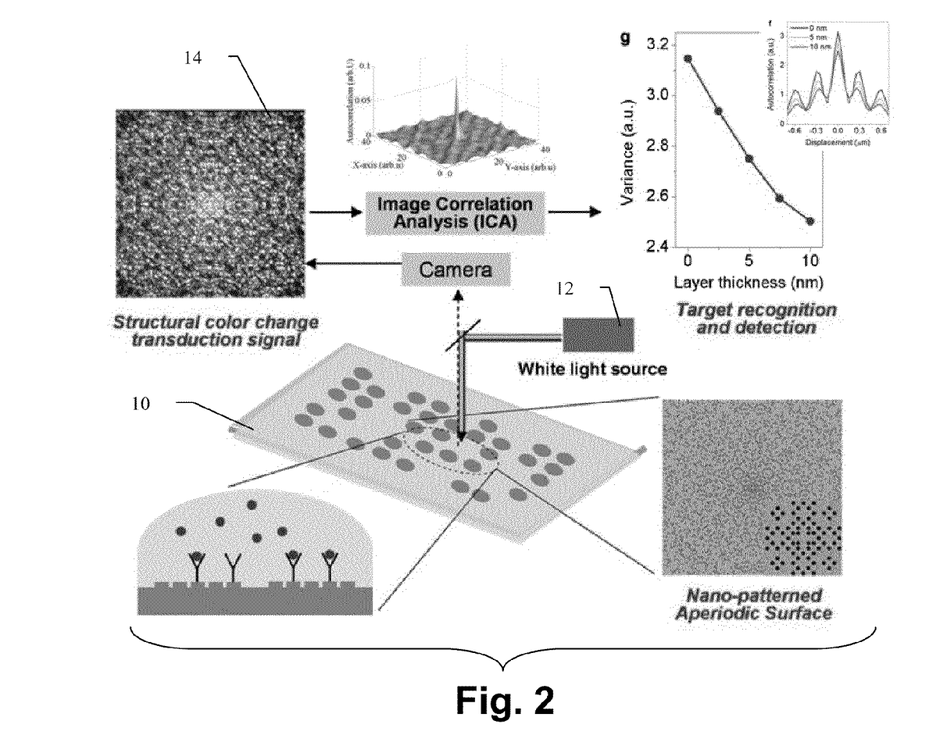

FIGS. 1 and 2 show simplified schematic diagrams of a colorimetric sensor based on an aperiodically nano-patterned planar surface. Illumination light is brought in at almost grazing incidence (x-y plane) and it is detected perpendicularly along the z axis. Due to the presence of characteristic spatially organized and localized color patterns in aperiodic structures, when an analyte (molecules, cells, etc) locally perturbs the refractive index of the surface, the colorimetric signatures changes accordingly and signals its presence.

As illustrated in FIG. 1, nano-patterned aperiodic surfaces (N-PASs) 10 can be illuminated by coherent/incoherent wide-spectrum light sources 12 at almost grazing incidence, and well-defined scattered colors and spatial colorimetric spatial patterns 14 appear in light collected from the top. The N-PAS active surfaces can be packaged by enclosing in a compact dark box with two apertures, one for illumination and one for colorimetric detection. At the collection aperture, a simple magnifying objective will enable the spatial resolution to observe well-defined colorimetric patterns. When made with a small size (<1 mm), N-PAS surfaces enable ultra-compact, low-weight colorimetric devices that can be utilized as mass sensors and color-change real-time responders for bio-chemical detection. The proposed sensing mechanism relies on the acquisition of angle-and spatial resolved scattering profiles of structural colors resonantly induced by multiple scattering in nanoscale, non-periodic surfaces patterned on the nanoscale. The local perturbation of the refractive index of the surface induced by the nano-patterning induces highly structured colorimetric signatures in the form of spatially and angularly localized scattered fields. The proposed sensing mechanism is originated by multiple light scattering in nano-patterned metal and dielectric surfaces, which act as "fingerprinting" multi-color diffraction gratings suitable for highly parallel sensing, where each colored areas of the device can be addressed separately. Quantification of pattern change in the intensity distribution of scattered radiation will occur through conventional correlation imaging techniques. The unique advantages of the proposed approach are related to the large dynamic range of scattered intensities combined with the highly parallel and multiplexing capabilities offered by the spatial localization of different chromatic components on the active surface. In addition, the nature of this sensing mechanism (spatially-localized color pattern change) makes it compatible with both label-free sensing and selective functionalization schemes using antibodies and standard chemical procedures.

In particular, miniaturized, optically transparent N-PASs can be used to enable high-throughput, parallel detection of bacteria, viruses, proteins and cells interactions, and their fingerprinting colorimetric signatures can be used to monitor the dynamics of a large number of bio-molecular interactions using a small volume of reagents.

In addition, N-PASs sensor structures are compatible with current microarray-based infrastructures that are most widely used for high throughput bimolecular interaction analysis. The proposed approach has several unique advantages with respect to traditional optical sensing schemes based on single color resonant diffraction grating platforms and frequency shifts of resonant modes in photonic structures. The N-PAS approach, which relies on highly structured color localization in nano-patterned aperiodic surfaces, offers a novel principle for the real-time, multiplexed bio-detection using simultaneous detection of spectral, spatial and angular distributions of scattered chromatic components (structural color change) which are highly sensitive to small local variations in the refractive index of the active surface.

As depicted in FIG. 2, the aperiodic sensing surfaces can be utilized within a compact, small volume enclosure, which accommodates the micrometer-millimeter scale surface on a variable angle horizontal stage. A coherent (super-continuum source) or coherent white light source or a laser beam illuminates the surface at an adjustable angle with a collimated beam of size larger or equal to the sensing surface. A collection aperture with imaging and magnifying optics (objectives) may be positioned such that spatial resolution will enable the unambiguous observation of the organized colorimetric patterns or tracking the changes in the resonant spectral characteristics. Spatial color change is detected by real time image correlation analysis on the acquired scattered intensity, and compared to a reference surface (not exposed to the analyte agents). The small size (<1 mm) of aperiodic nano-patterned sensors enables ultra-compact, low-weight colorimetric devices that can be utilized as mass, fluorescence and Raman sensors for real-time monitoring of bio-chemical processes.

Figure 3:
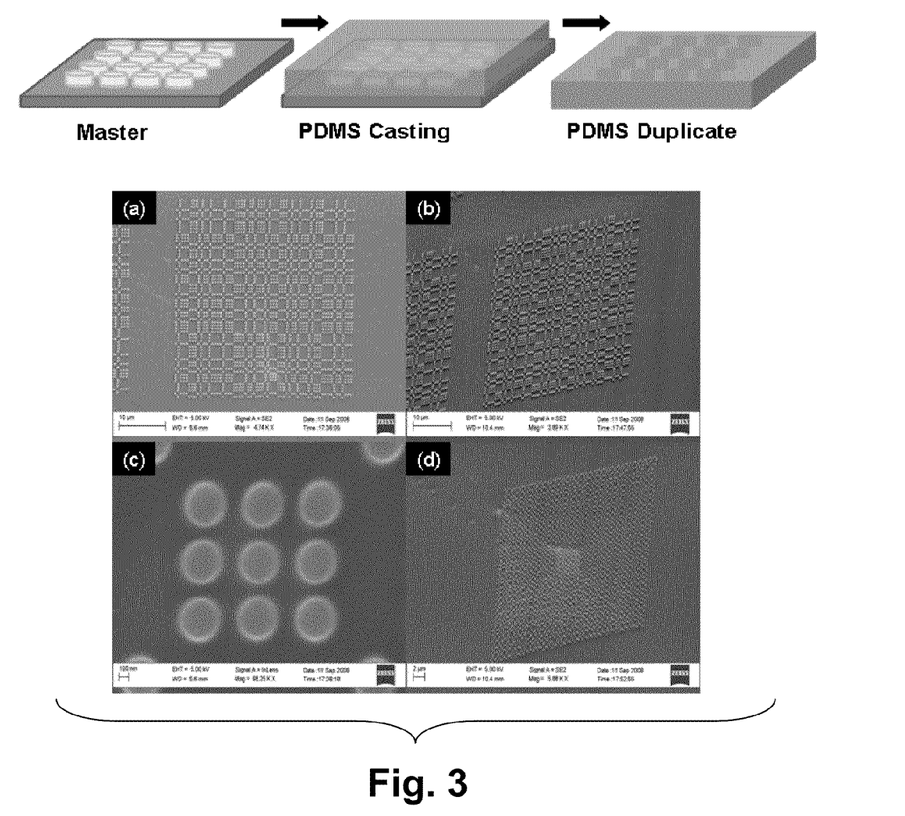
FIG. 3 is a schematic illustration of the replication of nanopatterned aperiodic surfaces (N-PASs) on polydimethylsiloxane (PDMS) thin films using a pattern transfer process, along with scanning electron microscope (SEM) images of resulting surfaces.

N-PAS sensors may be fabricated by e-beam lithography on large areas (1 mm$^2$) and they can be replicated on soft PDMS and PMMA transparent polymers by standard room temperature nano-imprinting. FIG. 3 shows the replication of nanoscale N-PASs on PDMS thin films using a pattern transfer process. FIG. 3 also includes scanning electron microscope (SEM) images at varying magnifications of nano-patterned PDMS surfaces showing an imprinted Rudin-Shapiro aperiodic lattice with 50 nm minimum feature size (a)-(d).

Different aperiodic patterns can be utilized for N-PAS sensing based on, but not limited to, deterministic aperiodic: Fibonacci, Thue-Morse and Rudin-Shapiro, Penrose lattices, and prime number arrays, L-systems. In addition, novel aperiodic patterns can be generated by number-theoretic functions such as: co-prime function, Gaussian primes, Eisenstein's primes, Galois fields, primitive roots, quadratic residues sequences, Riemann's zeta and L-functions. All these can be utilized to deterministically generate aperiodic surfaces with different degrees of spatial complexity.

Figure 4:
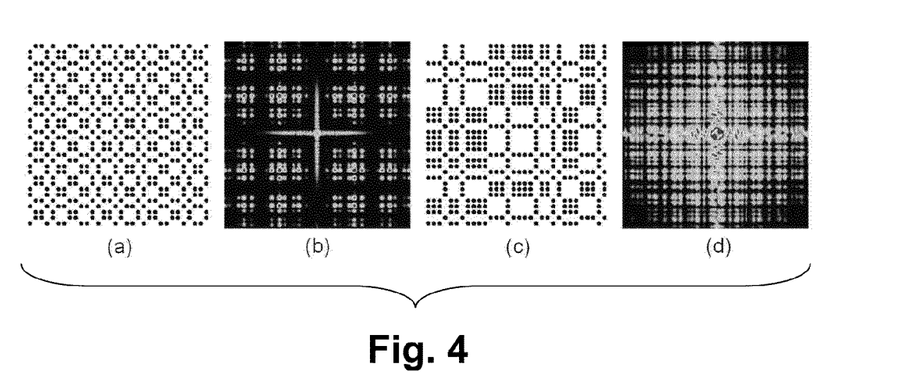
FIG. 4 shows real-space lattices of Thue-Morse and Rudin-Shapiro 2D photonic structures and their corresponding reciprocal space representations.

FIG. 4 shows real-space lattices of (a) Thue-Morse and (c) Rudin-Shapiro 2D photonic structures and their corresponding reciprocal space representations (lattice Fourier spectra) (b, d). The deterministic nature of the proposed aperiodic nano-patterned substrates makes them amenable to the design and optimization using traditional electromagnetic modeling techniques. A specific configuration of a sensor can be generated by arranging nano-particles or nano-holes according to simple deterministic algorithms based on the alternation of 1D aperiodic inflation maps along orthogonal directions. This approach uniquely specifies the positions of individual scatterers in the arrays once the minimum inter-particle separation has been chosen. As a result, the resulting DA photonic structures are long-range correlated, despite their lack of global translational invariance. Different aperiodic sensing substrates can be utilized based on, but not limited to, deterministic aperiodic: Fibonacci, Thue-Morse and Rudin-Shapiro, Penrose lattices, prime number arrays, L-systems, etc. In addition, novel aperiodic patterns can be generated by number-theoretic functions such as: co-prime function, Gaussian primes, Eisenstein's primes, Galois fields, primitive roots, quadratic residues sequences, Riemann's zeta and L-functions. In one example, a Thue-Morse array (FIG. 4(a)) may be generated by a 2D generalization of the aperiodic inflation: A→AB, B→BA, where A and B stand for the presence or the absence of a scatterer in a unit cell of side length a, respectively. Thue-Morse arrays are characterized by singular-continuous Fourier transforms (FIG. 4(b)). The inflation rule used to generate a Rudin-Shapiro array (FIG. 4(c)) can be obtained by the iteration of the two-letter inflation as follows: AA→AAAB, AB→AABA, BA→BBAB, BB→BBBA.

Figure 5:
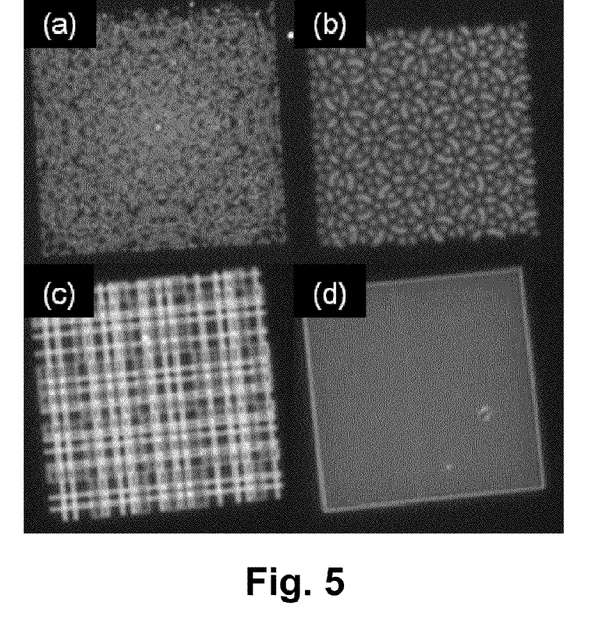
FIG. 5 shows dark-field images of aperiodic colorimetric signatures.

FIG. 5 shows dark-field images of aperiodic colorimetric signatures in (a) Gaussian prime lattice; (b) Penrose lattice; (c) Rudin-Shapiro lattice; (d) periodic lattice of nano-holes in optically transparent quartz. The structures have been illuminated by a white light source at grazing incidence, and the colorimetric signature is acquired in the perpendicular direction. The images in FIG. 5 have been acquired by a CCD camera using white light illumination in a dark-field microscope, and clearly demonstrate highly structured color localization on N-PAS surfaces.

The images of FIG. 5 provide striking examples of colorimetric signatures in periodic and deterministic aperiodic nano-patterns quartz surfaces. It is clear that periodic diffraction patterns (FIG. 5(d)) are fundamentally limited to homogeneous scattering intensity over the sensor areas (corresponding to only one well-defined periodicity) while aperiodic deterministic surfaces (FIGS. 5(a)-5(c)) give rise to spatially localized and highly organized color patterns which are fingerprinting multi-frequency sensing elements. FIG. 5 clearly demonstrates the unique advantage of the proposed approach, which offers highly structured color distributions for both spatial and frequency analysis. We also notice that the spatial color distributions (colorimetric signatures) of aperiodic surfaces additionally depends on the choice of the detection angle, which represents another parameter for multi-parametric detection schemes based on the spatial, angular and frequency responses.

It is noted that colorimetric signatures depend on the separation between the scattering particles (or voids). Best colorimetric effects are obtained by considering inter-particle separations in the range 50 nm-500 nm. This separation is defined edge-to-edge. The dimensions of the scattering nano-particles can vary between 100 nm-300 nm and the materials can be either metallic or dielectric.

Design and Fabrication of Nano-patterned Aperiodic Sensor Platforms

Figure 6:
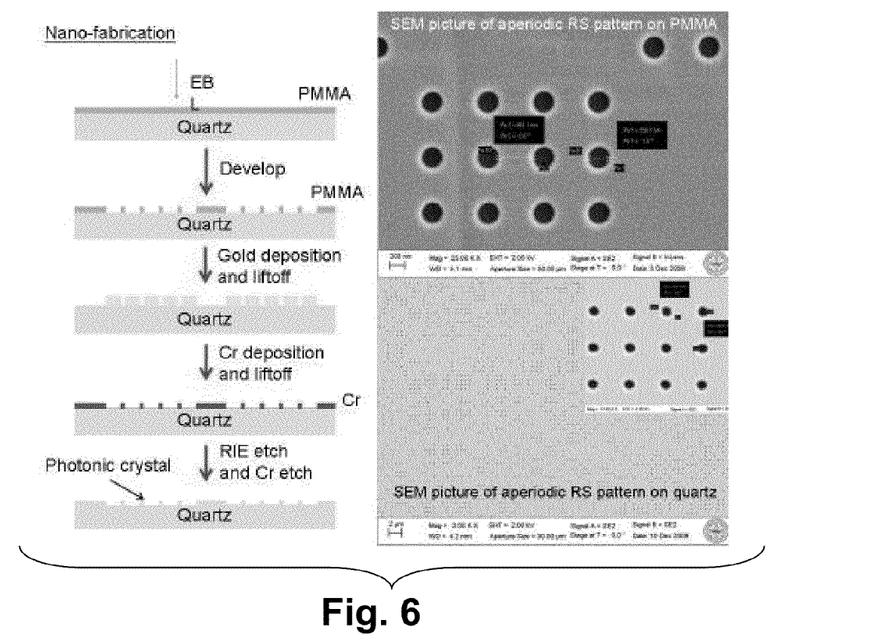
FIG. 6 shows a schematic of a process flow for hard mask (master) nanofabrication, along with SEM pictures of an aperiodic Rudin-Shapiro lattice written on PMMA polymer (top) and quartz (bottom)

FIG. 6 shows (at left side) a schematic of a process flow that can be used for hard mask (masters) nanofabrication. The right side of FIG. 6 shows SEM pictures of an aperiodic Rudin-Shapiro lattice written on PMMA polymer (top right) and quartz (bottom right). These substrates can be used for colorimetric sensing and cost-effective replication on functionalized transparent polymers.

The example fabrication process in FIG. 6 (left side) includes the following steps: 1) e-beam fabrication of nanoscale features (particles, etc) with aperiodic arrangements on a photo resist spin-coated on a substrate (such as transparent quartz, etc); 2) development; 3) gold metallization; 4) hard-metal deposition (i.e. Cr, etc); and 5) reactive ion etching and lift-off to transfer the pattern into the substrate material. Examples of nano-patterned surfaces fabricated using this simple process on quartz and PMMA transparent substrates are also shown in FIG. 6 to demonstrate the reduction to practice. The aperiodic nano-patterned structures have also been replicated on soft PDMS and PMMA transparent polymers by standard room temperature nano-imprinting. Preliminary results showing the replication of nanoscale aperiodic surfaces on PDMS thin films are shown in FIG. 3, along with a simple illustration of a pattern transfer process that has been utilized.

Detection Mechanisms

The general transduction mechanisms in nano-fabricated aperiodic sensors include: (a) shift of resonant peaks in the scattering cross sections of nano-patterned substrates; (b) changes in the angular scattering distributions (differential scattering cross sections) and corresponding changes in the intensity of the back-scattering cross-sections; (c) changes in the spatial color distribution in the far-field patterns; (d) enhanced fluorescence from the target material; (e) Raman signal from the target material; (f) changes in the material absorption characteristics.

Label-free Sensing by Monitoring Shifts of Resonant Spectral/Angular Features

Broadband resonant features can be observed in the frequency scattering spectra of aperiodic gratings if the incident angle and the frequency of the incoming field are tuned to achieve efficient coupling with quasi-stationary waves confined in the aperiodic gratings, which are formed by multiple scattering at several length scales in the grating plane. Remarkably, the same structures (fabricated either in metal or dielectric material platforms) can produce narrow-linewidth resonant peaks in their back-scattering spectra. Spectral shifts of these resonant peak induced by the changes in the grating nano-environment can serve as an optical transduction signal in grating-based biosensor platforms.

Figure 7:
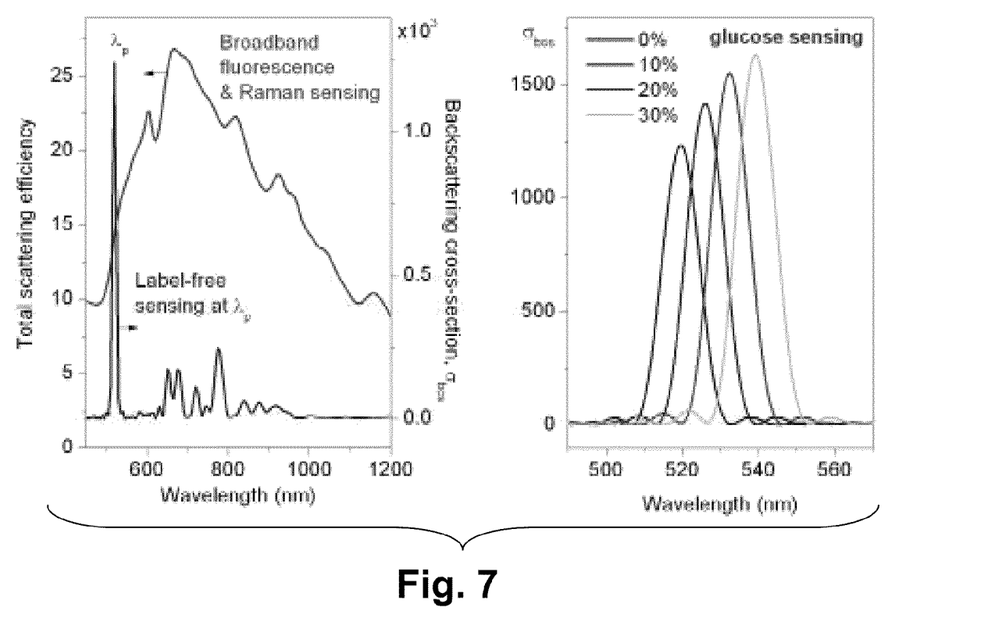
FIG. 7 shows plots of scattering efficiency and scattering cross section as functions of wavelength.

FIG. 7 shows certain results of simulations of a plane wave scattering on a Gaussian prime array of Au nano-spheres. In particular, FIG. 7 (left) shows back-scattering cross-section and total scattering efficiency of a Gaussian prime aperiodic grating composed of gold nano-particles immersed in water. Successively greater red-shifts of these peaks occur with increasing refractive index of the ambient glucose solution. The shift of the narrow-band resonance in the back-scattering spectrum can be used for tracking the changes in the grating nano-environment caused by varying the glucose concentration in the host medium (right). At the same time, the broadband total scattering spectrum is accompanied by the broadband near-field intensity spectrum, and can be exploited for fluorescence and Raman detection of biological targets.

Figure 8:
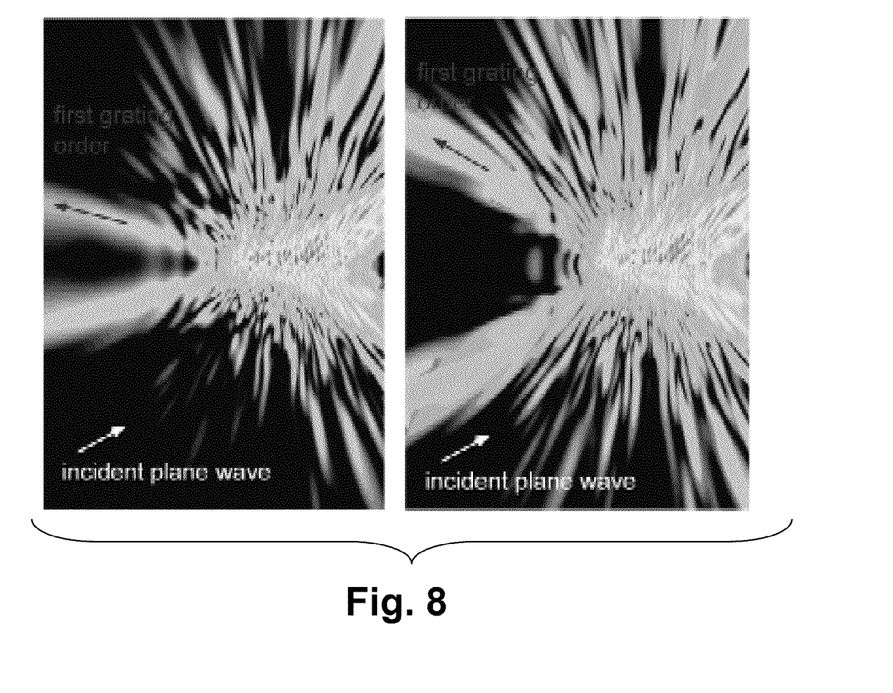
FIG. 8 is a diagram depicting changes in angular scattering distribution of a Gaussian prime grating of Au nano-particles in a glucose solution.

Alternatively, changes in the angular scattering distribution of light scattered by aperiodic nano-patterned surfaces with the changes of the ambient refractive index can be monitored. This is demonstrated in FIG. 8 which shows tracking of the angular position of the first grating order (dark arrow) in the angular scattering profile of the Gaussian prime nano-structure (in particular changes in the angular scattering distribution of the Gaussian prime grating of Au nano-particles in the glucose solution in water at a single wavelength (500 nm) with the change of the glucose concentration).

Image-correlation Sensing with Aperiodic Gratings

Another proposed sensing mechanism relies on the acquisition of angle-and spatial resolved scattering profiles of structural colors resonantly induced by multiple scattering from non-periodic surfaces patterned on the nanoscale (see FIG. 5). The local perturbation of the refractive index of the surface induced by the nano-patterning yields highly structured colorimetric signatures in the form of spatially and angularly localized scattered fields. The proposed sensing mechanism is originated by multiple light scattering in nano-patterned metal and dielectric surfaces, which act as "fingerprinting" multi-color diffraction gratings suitable for highly parallel sensing, where each colored area of the device can be addressed separately. Nano-patterned aperiodic sensors can be illuminated by coherent/incoherent wide-spectrum light sources at almost grazing incidence, and well-defined scattered colors and spatial colorimetric spatial patterns appear when collected from the top. Quantification of pattern change in the intensity distribution of scattered radiation can be achieved by using conventional correlation imaging techniques. Namely, we use the 2D image autocorrelation analysis to reveal the small changes in the intensity pattern due to the presence of biological material on the sensor surface. To construct the image autocorrelation function (ACF), the value of the field intensity at point (x, y) in the array plane is compared with that at another point (x', y') and mapped as a function of the distance between the two points. To quantify the change in the pattern induced by the presence of thin molecule layers, in FIG. 2 is plotted the variance of the fluctuations in the intensity distribution function, which can be found as the value of the properly normalized discrete ACF in the limit of zero lateral displacements. It can be seen that the absorption of the 2.5 nm-thin low-index dielectric (n=1.5) layer on the surface of the Gaussian prime nanostructure results in the 6.6% change in the absolute value of the intensity pattern variance, offering a possibility of robust sensing of the thickness changes in the nm- and sub-nm range. We note that the colorimetric signatures critically depend on the separation between the scattering particles (or voids). Best colorimetric effects are obtained by considering edge-to-edge inter-particle separations in the range of 50 nm-500 nm. The dimensions of the scattering nanoparticles can vary between 100 nm-300 nm, and the materials can be either metal or dielectric.

Label-free Sensing with Critical Modes of Aperiodic Photonic Structures

Another novel sensing mechanism offered by aperiodic photonic structures relies on the in-plane excitation (e.g., via a planar integrated waveguide or through a prism coupling) and spectral tracking of critical modes supported by such structures. Critical modes are spatially quasi-localized field states that, unlike the exponentially-localized Anderson modes in disordered media, decay weaker than exponentially and may show a rich behavior with self-similar fluctuations extending across their spatial structures.

Figure 9:
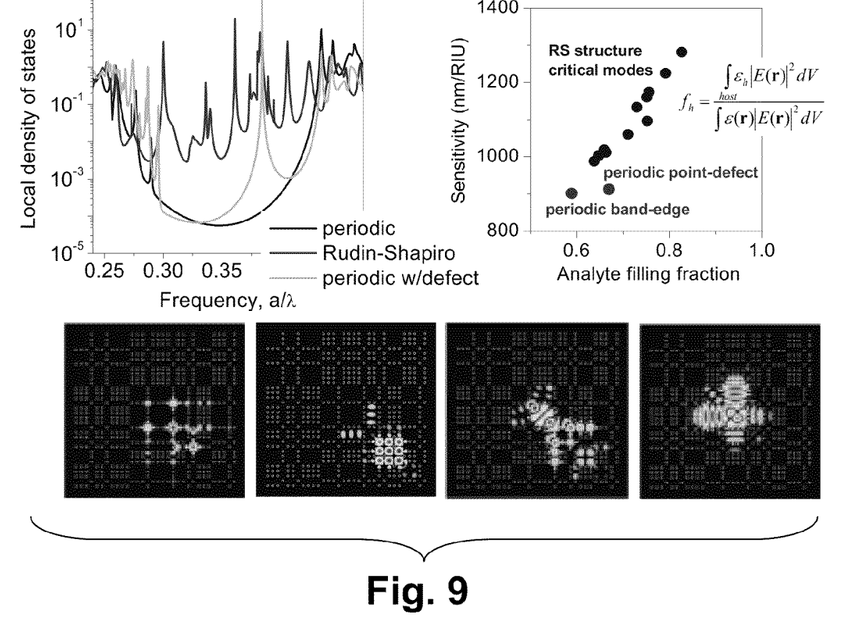
FIG. 9 shows plots of a spectrum of high-Q critical modes in a Rudin-Shapiro aperiodic photonic structure and near-field intensity patterns of quasi-localized critical modes.

FIG. 9 (top left) shows a spectrum of high-Q critical modes in a Rudin-Shapiro aperiodic photonic structure for the case of in-plane excitation. The bottom of FIG. 9 shows near-field intensity patterns of quasi-localized critical modes, and the top right shows a comparison of the sensitivity (the ratio of mode wavelength shift and the refractive index change) of the Rudin-Shapiro critical modes and the band-edge and localized defect modes of a periodic photonic crystal.

As demonstrated in FIG. 9 for the case of the Rudin-Shapiro photonic structure, in sharp contrast to the behavior of periodic photonic crystals, the optical spectrum of the RS structure features multiple peaks inside the photonic band-gap, which correspond to the excitation of the critical modes. The results of simulations show that the critical modes of aperiodic structures are more sensitive to the changes in the ambient refractive index than either band-edge or defect modes of periodic photonic crystals. This enhanced sensitivity has been attributed to a better overlap of the quasi-localized fields of critical modes with the analyte. Note that owing to the large number of high-Q critical modes that can be excited in aperiodic structures in a broad frequency range, the same structure with a fixed configuration can be used for sensing at different frequencies. Furthermore, our studies show that large aperiodic structures support high-Q critical modes that not only are characterized by different resonant frequencies but also have optical fields that are quasi-localized in different parts of the structure. As the mode frequency shift is caused only by the change of the refractive index in the area overlapping with the modal electric field, large aperiodic structures can be used as sensing arrays for simultaneous probing of different analytes at different operating frequencies.

4. Broadband SERS and fluorescence sensing platforms

Figure 10:
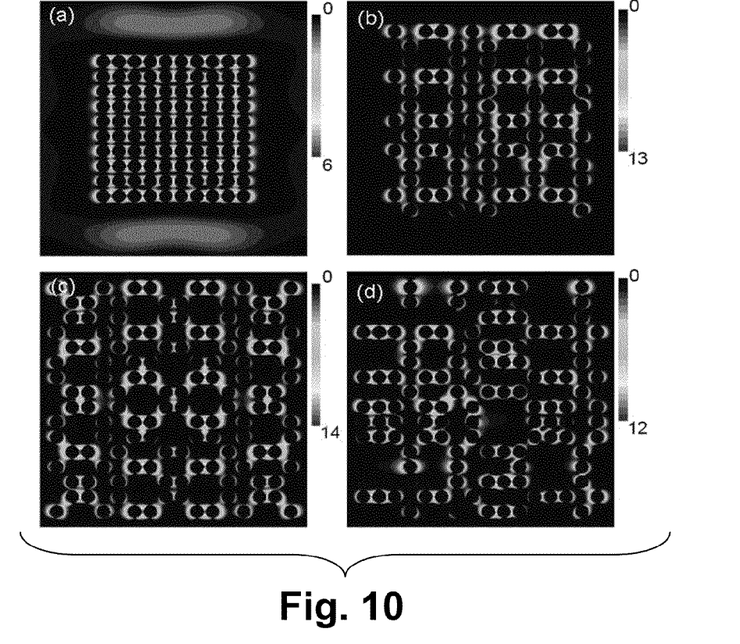
FIG. 10 shows calculated electric field distributions in the plane of (a) periodic (b) Fibonacci, (c) Thue-Morse, and (d) Rudin-Shapiro second-generation arrays of gold nano-spheres.

The long-range diffractive coupling of localized surface plasmon oscillations in aperiodic structures composed of noble-metal nanoparticles results in the formation of high-intensity hot-spots in the structure near-field across a wide frequency range. This can be observed in FIG. 10, which shows calculated electric field distributions in the plane of (a) periodic (b) Fibonacci, (c) Thue-Morse, and (d) Rudin-Shapiro second-generation arrays of gold nanospheres of 75 nm radii and 25 nm minimum inter-particle separation under the plane wave illumination at $\lambda$=785 nm with the E-field polarization parallel to the x-axis. This ability of aperiodic plasmonic arrays to generate highly localized intense hot-spots can be exploited in the design of robust and efficient SERS substrates.

Figure 11:
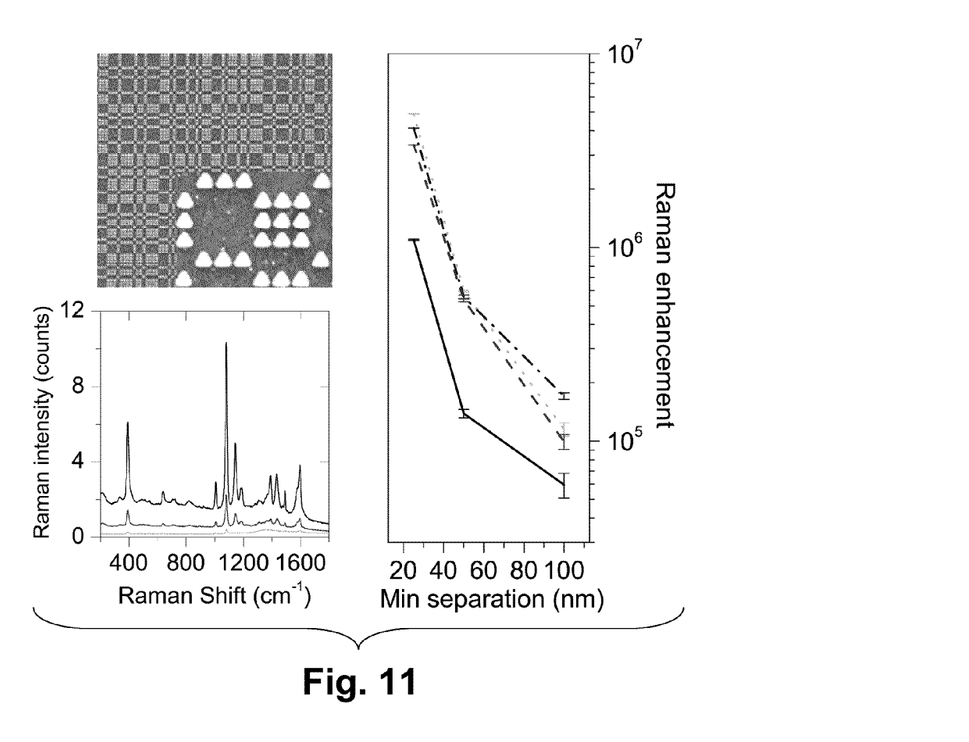
FIG. 11 shows a nanofabricated Rudin-Shapiro array of Au equilateral nano-triangles along with experimental SERS spectra of pMA and Raman enhancement factors on RS arrays with varying inter-particle gaps.

FIG. 11 (top left) shows nanofabricated Rudin-Shapiro array of Au equilateral nano-triangles with 200 nm side length and 25 nm minimum inter-particle separation. The bottom left shows experimental Stokes SERS spectra of pMA and Raman enhancement factors on RS arrays of Au nano-triangles with varying inter-particle gaps, and the right side shows enhancement factors calculated from the experimental SERS spectra of periodic and aperiodic nano-triangle arrays: Periodic (solid, black), Fibonacci (dot, green), Thue-Morse (dash-dot, blue), and Rudin-Shapiro (dash, red). The broadband controllable modification of the local density of states on both plasmonic and photonic nano-patterned structures can also be exploited in sensors based on different physical detection mechanisms, such as enhanced material absorption or fluorescence.

Figure 12:
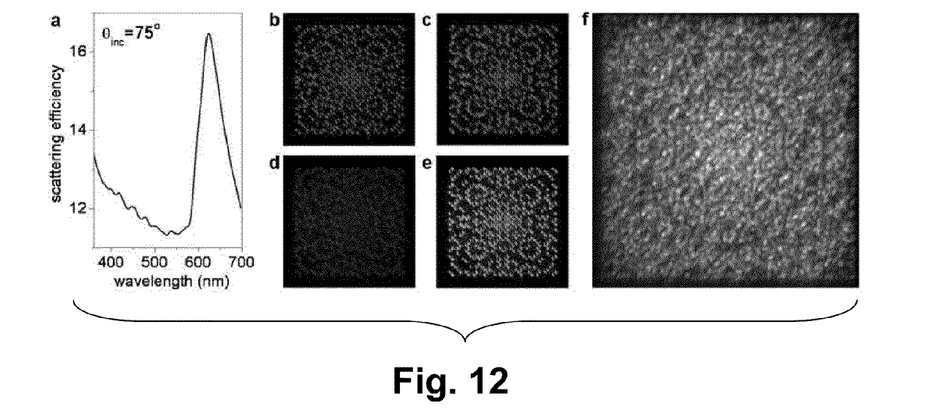
FIG. 12 shows colorimetric color formation in aperiodic arrays.

FIG. 12 shows colorimetric color formation in aperiodic arrays: (a) Calculated scattering spectrum of a Gaussian prime array of 100 nm-radius Cr nanospheres with 300 nm nearest center-to-center separation illuminated by a plane wave at 75 degrees to normal. Also shown are calculated spatial field distributions (top view) of the scattered light in the plane of an array at (b) λ=470 nm (blue), (c) λ=520 nm (green), (d) λ=630 nm (red), and (e) a combined RGB image (the images are overlapped with weighted amplitudes to properly represent their spectral contributions). At (f) is shown the corresponding measured image of the Gaussian prime nanoparticle array illuminated at a grazing incidence with white light.

Figure 13:
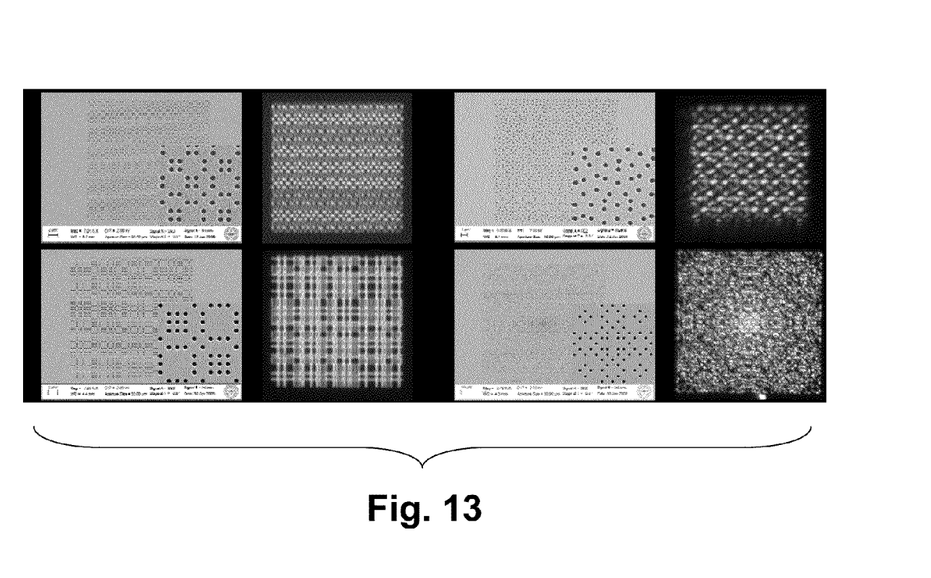
FIG. 13 shows SEM images and colorimetric signatures of 2D aperiodic gratings.

FIG. 13 shows SEM images and colorimetric signatures of 2D aperiodic gratings, namely nano-patterned aperiodic lattices of 100 nm-radius and 70 nm-deep cylindrical indentations on a quartz substrate: (a) Thue-Morse lattice (nearest center-to-center separation d=400 nm), (c) Rudin-Shapiro lattice (d=400 nm), (e) Penrose lattice (d=400 nm), and (g) Gaussian prime lattice (d=300 nm). Images (b, d, f, h) are dark-field microscopy images of corresponding aperiodic gratings.

Figure 14:
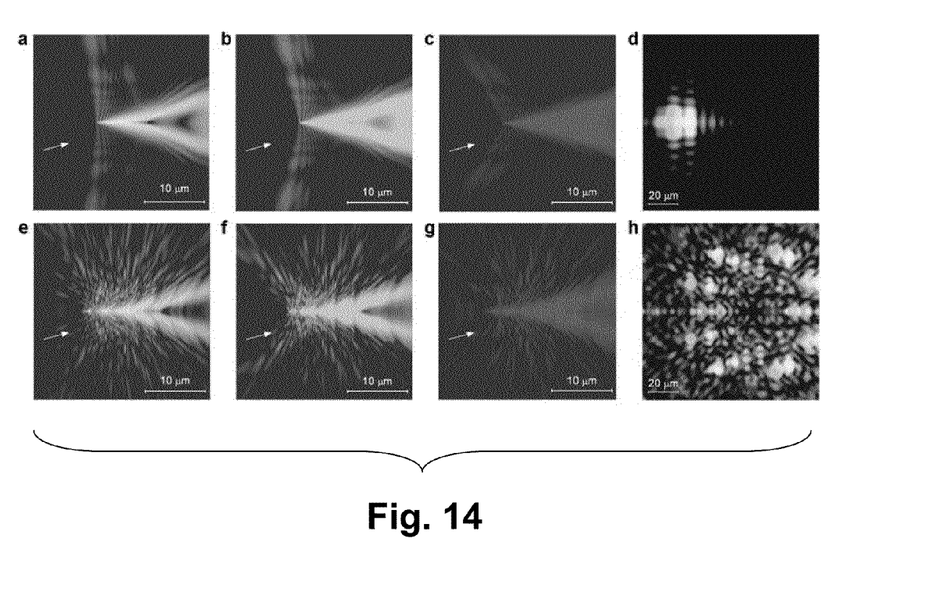
FIG. 14 shows angular profiles of light scattered by the periodic and Gaussian Prime gratings.

FIG. 14 shows angular profiles of light scattered by the periodic and Gaussian Prime gratings. Spatial field distributions (side view) of the light scattered by a periodic array of 100 nm-radius nano-spheres with refractive index n=1.5 separated by 200 nm gaps (d=400 nm) illuminated by a plane wave at θinc=75 o and a, λ=470 nm (blue), b, λ=520 nm (green), c, λ=630 nm (red) The direction of the incident field is indicated with a white arrow. d, Multi-wavelength scattered field distribution (top view) at 100 μm above the periodic grating within the collection cone (±30 o) of the microscope objective with N.A.=0.5. e-h, same as a-d for a Gaussian prime array with 300 nm nearest center-to-center separation between spheres.

Figure 15:
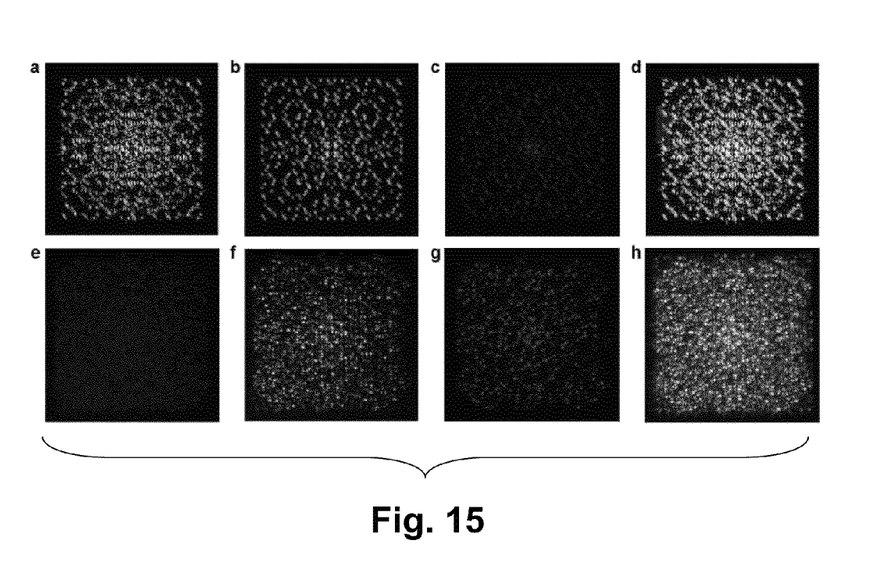
FIG. 15 shows structural color formation in aperiodic arrays.

FIG. 15 shows structural color formation in aperiodic arrays. Calculated spatial field distributions (top view) of the scattered light in the plane of a Gaussian prime array of nanospheres with 300 nm nearest center-to-center separation at (a) λ=470 nm (blue), (b) λ=520 nm (green), (c) λ=630 nm (red), and a combined RGB image. Experimentally measured dark-field images of the nano-patterned gratings with the Gaussian prime lattice under (e) blue, (f) green, (g) red, and (h) white light illumination.

Figure 16:
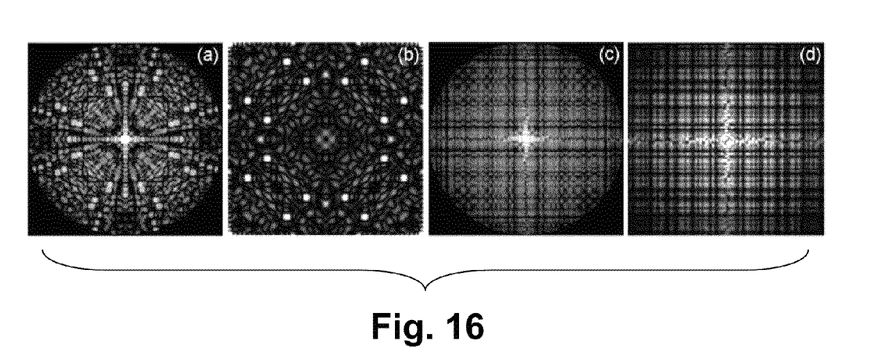
FIG. 16 shows far-field colorimetric signatures of aperiodic gratings.

FIG. 16 shows far-field colorimetric signatures of aperiodic gratings. Simulated far-field multi-color scattered intensity maps of (a) Gaussian prime and (c) Rudin-Shapiro arrays of 200 nm-diameter nano-spheres and (b,d) the corresponding lattices Fourier transforms.

While various embodiments of the invention have been particularly shown and described, it will be understood by those skilled in the art that various changes in form and details may be made therein without departing from the spirit and scope of the invention as defined by the appended claims.

What is claimed is:

1. Apparatus, comprising:
a substrate having a surface with a deterministic, aperiodic nano-scale pattern, the pattern extending across an area to be covered by an analyte whose presence is to be detected during use of the apparatus, the pattern exhibiting deterministic aperiodicity and corresponding dense filling of reciprocal space across the entirety of the area;
a source of light directed at the surface of the substrate;
a detector operative to receive a pattern of light scattered off the surface of the substrate and to convert the received pattern of light to a corresponding color image, the color image having a colorimetric spatial distribution pattern; and
image processing circuitry operative to perform pattern recognition on the colorimetric spatial distribution pattern to detect the presence of the analyte on the surface of the substrate.

2. Apparatus according to claim 1 wherein the pattern of light scattered off the surface of the substrate reflects phase-sensitive modifications of a structural color pattern.

3. Apparatus according to claim 2 wherein the modifications are interrogated by measuring scattered radiation in the form of color patterns which are colorimetric fingerprints specific to nanostructured surfaces with aperiodic patterns.

4. Apparatus according to claim 3 wherein the measuring of the scattered radiation employs dark-field microscopy.

5. Apparatus according to claim 1 wherein the detector and image processing circuitry make up a sensing transduction mechanism operating in both frequency domain and spatial domain by pattern recognition analysis.

6. Apparatus according to claim 5 wherein the pattern recognition analysis is selected from autocorrelation and wavelet-based analysis.

7. Apparatus according to claim 1 wherein spectral sensing occurs by monitoring frequency shifts of critical modes in aperiodic structures in response to a local refractive index change of the aperiodic structures.

8. Apparatus according to claim 1 wherein the deterministic, aperiodic nano-scale pattern includes Raman active metallic particles arranged on the surface, and further comprising Raman detection circuitry operative to detect a specific Raman signal from the surface concurrently with operation of the detection circuitry.

9. Apparatus according to claim 1 wherein the surface is selected from (a general dielectric material and a plasmonic surface with metal nanoparticles.

10. Apparatus according to claim 9 wherein the general dielectric material is a low-index material.

11. Apparatus according to claim 1 wherein the deterministic, aperiodic nano-scale pattern includes a nanopillar array.

12. Apparatus according to claim 1 wherein the deterministic, aperiodic nano-scale pattern is selected from quasi-periodic systems and more complex structures.

13. Apparatus according to claim 12 wherein the quasi-periodic systems are selected from Fibonacci, Gaussian primes, and Penrose lattices, and wherein the more complex structures are selected from Thue-Morse, Rudin-Shapiro, prime number arrays, Ulam's spirals, co-prime arrays, and Eisenstein's primes.

14. A method, comprising:
directing light at a surface of a substrate, the surface having a deterministic, aperiodic nano-scale pattern extending across an area to be covered by an analyte whose presence is to be detected, the pattern exhibiting deterministic aperiodicity and corresponding dense filling of reciprocal space across the entirety of the area;
detecting a pattern of light scattered off the surface of the substrate and converting the received pattern of light to a corresponding color image, the color image having a colorimetric spatial distribution pattern; and
performing pattern recognition on the colorimetric spatial distribution pattern to detect the presence of the analyte on the surface of the substrate.

15. A method according to claim 14 wherein the pattern of light scattered off the surface of the substrate reflects phase-sensitive modifications of a structural color pattern.

16. A method according to claim 15 further comprising interrogating the modifications by measuring scattered radiation in the form of color patterns which are colorimetric fingerprints specific to nanostructured surfaces with aperiodic patterns.

17. A method according to claim 16 wherein the measuring of the scattered radiation employs dark-field microscopy.

18. A method according to claim 14 wherein the detecting and performing pattern recognition employ a sensing transduction mechanism operating in both frequency domain and spatial domain by pattern recognition analysis.

19. A method according to claim 18 wherein the pattern recognition analysis is selected from autocorrelation and wavelet-based analysis.

20. A method according to claim 14 wherein spectral sensing occurs by monitoring frequency shifts of critical modes in aperiodic structures in response to a local refractive index change of the aperiodic structures.

21. A method according to claim 14 wherein the deterministic, aperiodic nano-scale pattern includes Raman active metallic particles arranged on the surface, and further comprising detecting a specific Raman signal from the surface concurrently with detecting the pattern of light from the substrate.

22. A method according to claim 14 wherein the surface is selected from (a general dielectric material and a plasmonic surface with metal nanoparticles.

23. A method according to claim 22 wherein the general dielectric material is a low-index material.

24. A method according to claim 14 wherein the deterministic, aperiodic nano-scale pattern includes a nanopillar array.

25. A method according to claim 14 wherein the deterministic, aperiodic nano-scale pattern is selected from quasi-periodic systems and more complex structures.

26. A method according to claim 25 wherein the quasi-periodic systems are selected from Fibonacci, Gaussian primes, and Penrose lattices, and wherein the more complex structures are selected from Thue-Morse, Rudin-Shapiro, prime number arrays, Ulam's spirals, co-prime arrays, and Eisenstein's primes.

* * * * *

UNITED STATES PATENT AND TRADEMARK OFFICE
CERTIFICATE OF CORRECTION

PATENT NO. : 8,339,597 B2
APPLICATION NO. : 13/192757
DATED : December 25, 2012
INVENTOR(S) : Luca Dal Negro et al.

It is certified that error appears in the above-identified patent and that said Letters Patent is hereby corrected as shown below:

On the title page item:

"(73) Assignee: Trustees of Boston University, Boston, MA (US)" should read

--(73) Assignee: Trustees of Boston University, Boston, MA (US) and
Tufts University, Medford, MA (US)--

Signed and Sealed this
Twenty-third Day of July, 2013

Teresa Stanek Rea
*Acting Director of the United States Patent and Trademark Office*